(12) United States Patent
Katayama et al.

(10) Patent No.: US 7,368,099 B2
(45) Date of Patent: May 6, 2008

(54) MRI CONTRAST AGENTS

(75) Inventors: Yoshiki Katayama, Fukuoka (JP);
Hiroaki Shimokawa, Fukuoka (JP);
Tatsuhiro Yamamoto, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 10/546,964

(22) PCT Filed: Feb. 3, 2004

(86) PCT No.: PCT/JP2004/001063

§ 371 (c)(1),
(2), (4) Date: Aug. 26, 2005

(87) PCT Pub. No.: WO2004/075925

PCT Pub. Date: Sep. 10, 2004

(65) Prior Publication Data

US 2006/0153773 A1    Jul. 13, 2006

(30) Foreign Application Priority Data

Feb. 27, 2003 (JP) ............................. 2003-050574
Sep. 16, 2003 (JP) ............................. 2003-322515

(51) Int. Cl.
*A61B 5/055* (2006.01)
*A61K 49/00* (2006.01)

(52) U.S. Cl. .................. 424/9.36; 424/9.1; 424/9.3

(58) Field of Classification Search ............. 424/9.36
See application file for complete search history.

(56) References Cited

U.S. PATENT DOCUMENTS

2004/0204344 A1* 10/2004 Huang ..................... 514/6

FOREIGN PATENT DOCUMENTS

WO    WO0074727 A2 * 12/2000

OTHER PUBLICATIONS

Yamamoto et al. (Analytical Sciences 2004, 20, 5-7).*
Dezutter et al. (Nucl. Med. Comm. 2001, 22, 553-558).*

* cited by examiner

*Primary Examiner*—Michael G. Hartley
*Assistant Examiner*—Melissa Perreira
(74) *Attorney, Agent, or Firm*—Fay Sharpe LLP

(57) ABSTRACT

An MRI contrast agent enables direct detection and imaging of exfoliated vascular endothelial sites. The MRI contrast agent includes an imaging unit which contains an unpaired electron-carrying atom and/or molecule and is capable of amplifying or reducing MRI signals, and a detection unit which is bonded to the imaging unit and is capable of selectively recognizing exfoliated vascular endothelial sites and binding thereto. The detection unit is exemplified by one having a chemical structure expressed by the following formula (I), wherein at least one of $R_1$-$R_{11}$ is, for example, a sulfonic acid group, and X is, for example, a phenyl group which may be substituted:

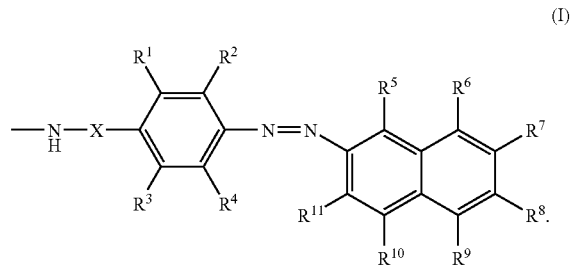

(I)

2 Claims, 5 Drawing Sheets

MRI CONTRAST AGENTS

TECHNICAL FIELD

The present invention belongs to the field of in vivo reagent, and particularly relates to a novel contrast agent for use in MRI.

BACKGROUND ART

In MRI (Magnetic Resonance Imaging), an intravascular contrast agent is used to ensure high-contrast images. Conventional intravascular MRI contrast agents are dedicated to observation of an overall vascular silhouette, i.e., the degree of stricture in the vascular lumen to provide information for the diagnosis and treatment of vascular diseases, and they cannot be applied for directly detecting lesion sites where the vascular endothelia have exfoliated.

The ability to image the exfoliated vascular endothelia directly as they are would greatly contribute to early disease detection and treatment. However, there are found almost no MRI contrast agents developed for such purpose. A method has been proposed for detecting injured or inflamed vascular sites, in which there are used antibodies against integrin or fibrin as targeting moiety in the MRI contrast agents (D. A. Sipkins et al., Nature Medicine, 4, 623-626 (1998); S. Flacke et al., Circulation, 104, 1280-1285 (2001)). However, such antibody-based contrast agents are not practical as they are costly because they require complicated steps to prepare and have to be used in a large amount.

The object of the invention is to provide a novel MRI contrast agent which enables direct detection and imaging of exfoliated vascular endothelial sites and which is easy to prepare and inexpensive to use.

DISCLOSURE OF THE INVENTION

Through extensive studies, the present inventors found substances which are capable of selectively recognizing exfoliated vascular endothelial sites and binding thereto, and achieved the present invention by combining a structural unit of such substance with a unit of imaging function.

Thus, according to the present invention there is provided a contrast agent for use in MRI, comprising an imaging unit which contains an unpaired electron-carrying atom and/or molecule and is capable of amplifying or reducing MRI signals, and a detection unit which is bonded to said imaging unit and is capable of selectively recognizing exfoliated vascular endothelial sites and binding thereto.

Specifically, the present invention provides an MRI contrast agent which is novel in that, differently from the conventional MRI contrast agents which are dedicated only to imaging the overall vascular silhouette, it is capable of directly detecting exfoliated vascular endothelial sites as they are, as well as imaging the sites.

A preferred but non-limiting example of the detection unit of the MRI contrast agent of the present invention is one having a chemical structure expressed by the following general formula (I):

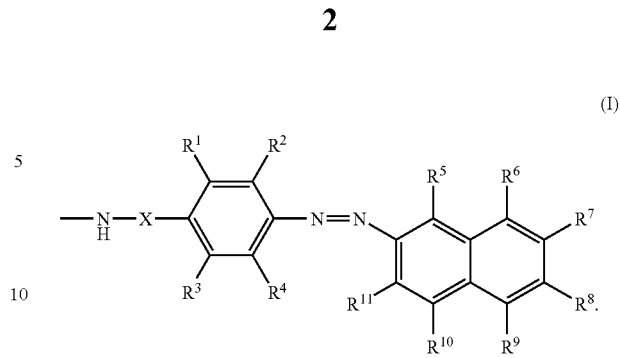

In the formula (I), at least one of $R^1$, $R^2$, $R^3$, $R^4$, $R^5$, $R^6$, $R^7$, $R^8$, $R^9$, $R^{10}$ and $R^{11}$ may be independently sulfonic acid group, hydroxyl group or amino group, at least one of $R^1$, $R^2$, $R^3$ and $R^4$ may be independently an alkyl group or alkoxy group having 1 to 3 carbon atoms, the remaining ones of $R^1$, $R^2$, $R^3$, $R^4$, $R^5$, $R^6$, $R^7$, $R^{8, R9, R10}$ and $R^{11}$ which do not fall within any of the above-mentioned functional groups are all hydrogen atoms, and X, if present, represents a phenyl group in which at least one site may be substituted with an alkyl group or alkoxy group having 1 to 3 carbon atoms.

In the chemical formulae as used in the present specification and drawings, carbon atoms or hydrogen atoms are sometimes omitted in accordance with the conventional practice.

The MRI contrast agents according to the present invention are of outstanding utility in the early detection and early treatment of vascular diseases because they are capable of selectively detecting exfoliated vascular endothelia. The MRI contrast agents of the present invention can be easily prepared through known synthetic reactions and are low-cost because they are effective when used in a relatively small quantity.

BEST MODE FOR CARRYING OUT THE

INVENTION

Figure 1:
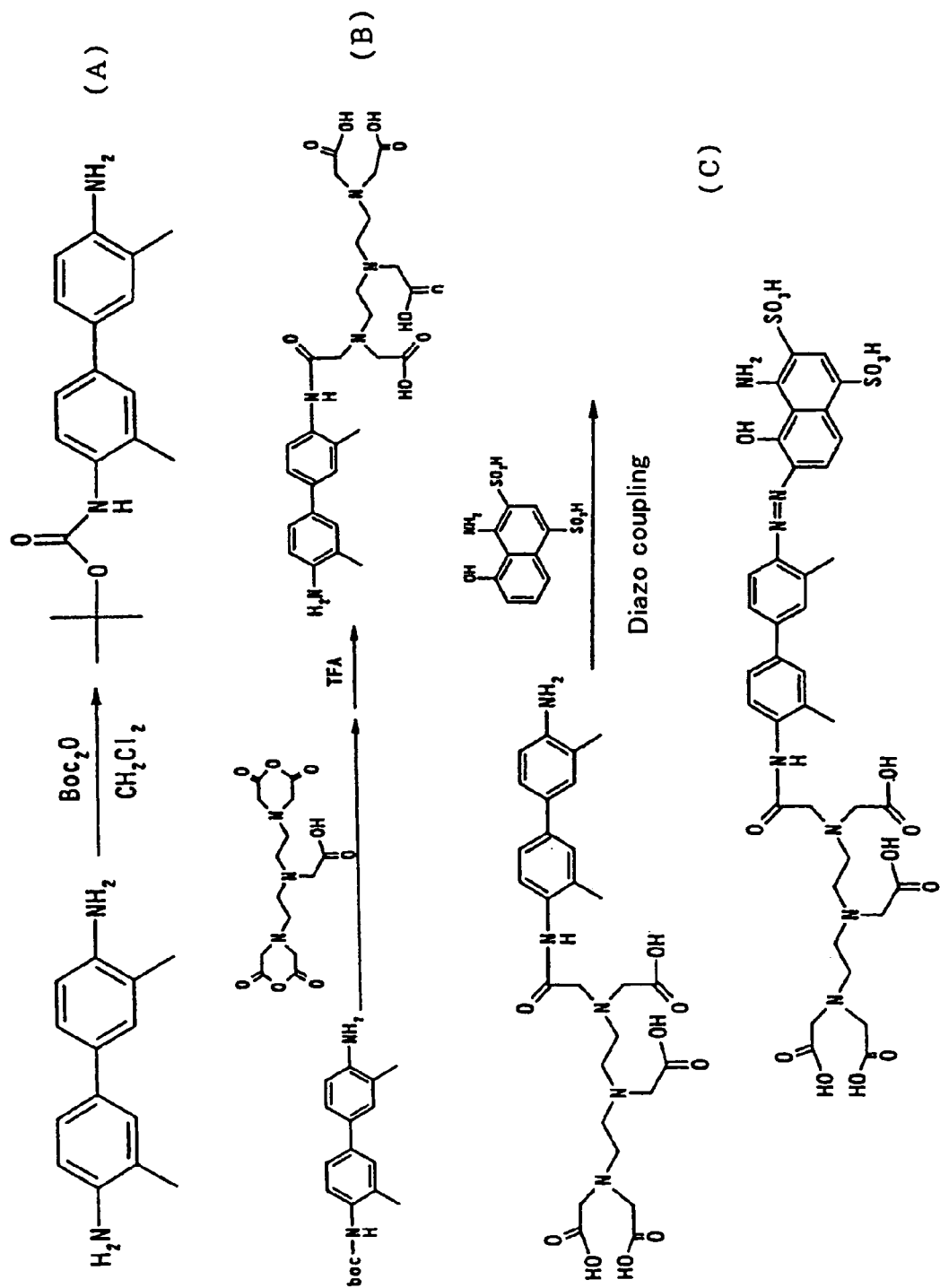
FIG. 1 shows a reaction scheme for synthesizing MRI contrast agents that are embodiments of the present invention.

In the formula (I) which expresses the chemical structure of a preferred example of the detection unit of the MRI contrast agent of the present invention, at least one of $R^1$, $R^2$, $R^3$, $R^4$, $R^5$, $R^6$, $R^7$, $R^8$, $R^9$, $R^{10}$ and $R^{11}$ (hereinafter referred to as $R^1$-$R^{11}$) may be independently sulfonic acid group (—$SO_3H$), hydroxyl group (—OH) or amino group (—$NH_2$). More specifically, either all of $R^1$-$R^{11}$ are hydrogen atoms (i.e. unsubstituted), or that at least one of $R^1$-$R^{11}$ is sulfonic acid group, hydroxyl group, or amino group. In a case where two or more of $R^1$-$R^{11}$ are sulfonic acid group, hydroxyl group or amino group, such two or more functional groups may be the same or different. It is generally preferable for realizing increased water-solubility of the MRI contrast agent of the present invention that at least one of $R^4$-$R^{10}$ is sulfonic acid group (particularly in a case where the imaging unit is of low hydrophilicity).

In addition, in the formula (I), at least one of $R^1$, $R^2$, $R^3$ and $R^4$ may be independently an alkyl group or alkoxy group having 1 to 3 carbon atoms, between which methyl group is particularly preferable. The remaining ones of $R^1$-$R^{11}$ which do not fall within any of the above-mentioned functional groups are all hydrogen atoms.

Furthermore, in the formula (I), X need not be present, in which case the benzene ring as shown in the formula (I) is directly bonded to —NH. X, if present, represent a phenyl group in which at least one site may be substituted with an alkyl or alkoxy group having 1 to 3 carbon atoms (preferably methyl group).

Thus, preferable examples of the chemical formula of the detection unit of the MRI contrast agent of the present invention include, but are not limited to, the following chemical formulae (II), (III), (IV), (V) and (VI):

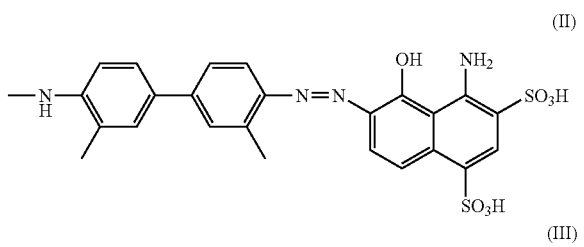

(II)

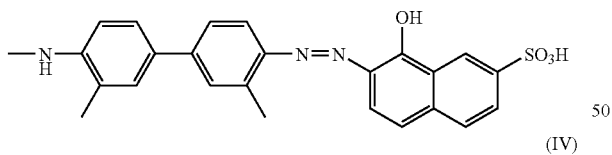

(III)

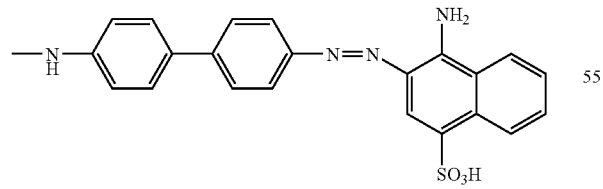

(IV)

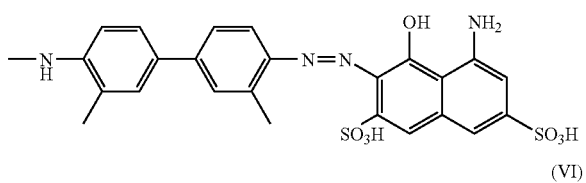

(V)

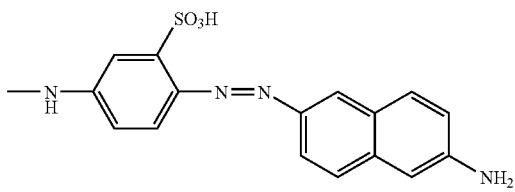

(VI)

There are no particular restrictions with respect to the imaging unit of the MRI contrast agent of the present invention, except that it is required to contain an unpaired electron-carrying atom and/or molecule and be capable of amplifying or reducing MRI signals. More specifically, as the imaging unit of the MRI contrast agent, there can be utilized a variety of known substances capable of enabling imaging in MRI due to a function such as that of shortening the relaxation time of protons ($T_1$, $T_2$). For example, there can be used a chelated complex of a paramagnetic metal ion such as $Gd^{3+}$, $Dy^{3+}$ $Eu^{3+}$, $Fe^{3+}$, $Mn^{2+}$; a nitroxide radical molecule such as a piperidine derivative and a pyrrolidine derivative; or a ferromagnetic material such as magnetite ($Fe_3O_4$). Particularly preferred is a chelated complex of gadolinium [Gd(III)] in which is used such compound as DTPA, DOTA or EDTA as the ligand.

Thus, as a preferable MRI contrast agent according to the present invention, there is exemplified, without limitation thereto, one expressed by the following formula (VII) in which the imaging unit is DTPA (diethylenetriaminepentaacetic acid) complex of Gd(III) and the detecting unit has the composition of the aforementioned chemical formula (II).

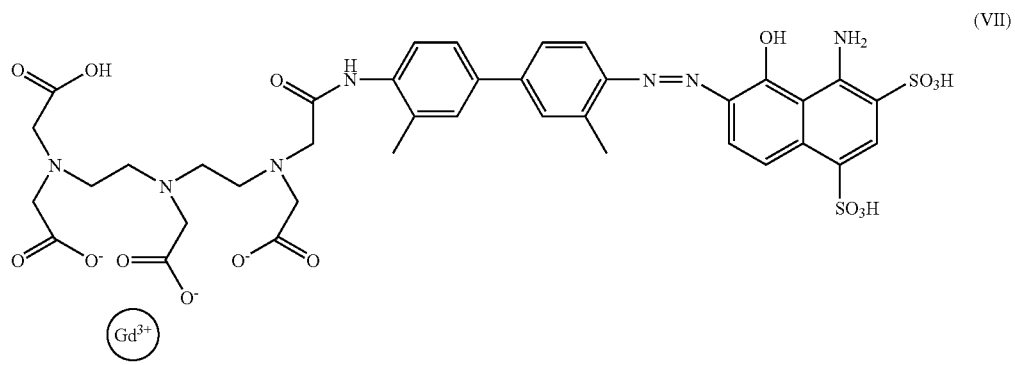

The MRI contrast agent of the present invention can be easily synthesized by appropriately modifying known reactions. For example, in a case where there is used as the imaging unit a metal complex such as gadolinium chelated complex, the desired MRI contrast agent can be obtained by introducing a Boc group into an amino compound (i.e. by t-butoxycarbonylating the amino compound) which corresponds to a portion of the detection unit expressed by the formula (I), allowing the resultant to react with the ligand portion of the metal complex, removing the Boc group, combining the resultant with the remaining portion of the detection unit through the diazo coupling, and subjecting the resultant to a complex formation with the metal (see the working example set out below).

The MRI contrast agent of the present invention thus obtained is capable of selectively recognizing exfoliated vascular endothelial sites (lesion sites) and binding thereto through the detection unit while enabling said sites to be visualized as MRI signals through the imaging unit. The MRI contrast agent of the present invention can therefore provide very reliable information in the treatment and diagnosis of vascular diseases, as a contrast agent specific to exfoliated vascular endothelial sites. For example, it is known that exfoliated vascular endothelial sites are unstable and arteriosclerosis will proceed more rapidly therein than in the sites without such exfoliation even if the degrees of the strictures are of the same level. The detection of exfoliated vascular endothelial sites using the MRI contrast agent of the present invention therefore contributes to early diagnosis and treatment of such circulatory diseases.

While working examples are set out below in order to more clearly define the features of the present invention, the present invention is not in any respect limited to such working examples.

EXAMPLES

Example 1

Synthesis of the Contrast Agent

In accordance with the reaction scheme as shown in FIG. 1, there was synthesized the MRI contrast agent of the present invention as expressed by the aforementioned formula (VII).

(1) Synthesis of Boc DMB (Step A).

Dimethylbenzidine (DMB) 1.0 g (4.71 mmol), dibutoxycarbonylketone ($Boc_2O$) 1.28 g (5.88 mmol) and triethylamine 0.714 g were added to 20 ml of dichloromethane, followed by stirring at room temperature for 48 hours. The reaction mixture was subjected to filtration, added with chloroform, and then washed with a saturated aqueous solution of L-sodium tartrate to remove unreacted DMB. The chloroform phase was subjected to concentration in vacuo, refining by silica gel chromatography, and then vacuum drying to obtain the desired product (0.60 g).

(2) Synthesis of DMB-DTPA (Step B).

Boc DMB 0.30 g (0.96 mmol) was dissolved in 20 ml of pyridine. In the resultant solution was suspended DTPA anhydride 0.343 g (0.96 mmol). The atmosphere of the container (round-bottom flask) was replaced with nitrogen gas and the flask was sealed, followed by stirring the contents thereof overnight at 50° C. The unreacted DTPA anhydride was removed by suction filtration. The filtrate was subjected to vacuum drying, added with 6 ml of 0.1 NaOH (0.6 mmol), allowed to stand for one hour, and then lyophilized. The resultant was dissolved in water, and the desired intermediate was fractionated by ODS/silica gel column chromatography. The fractionate was dissolved in 4 ml of TFA, and the solution was allowed to stand for thirty minutes and then added with ether 40 ml. The Boc group was removed by recovering the precipitate to obtain the desired product at a yield of 0.85 g.

(3) Diazo Coupling (Step C):

A diazonium salt was prepared by admixing DMB-DTPA 65 mg (62.3 μmol) and 35% HCl 16.5 μl (187 μmol) in 1 ml of water, and $NaNO_2$ 4.5 mg (65.2 μmol) was added to the mixture, followed by stirring for thirty minutes. Diazo coupling reaction was carried out by adding the salt dropwise into 1 ml of aqueous solution containing 21.2 mg (62.2 μmol) of monosodium 1-amino-8-naphthol-2,4-disulfonate and 26.4 mg (249 μmol) of $Na_2CO_3$, on an ice bath. Then, 35% HCl was added dropwise to the reaction mixture to obtain the desired product as the precipitate, at a yield of 42.5 mg.

(4) Complex Formation with Gadolinium:

A sample 19.8 mg of the product of the diazo coupling was dissolved in 2.2 ml of water. An equimolar amount of 1M $GdCl_3$ aqueous solution was added to the solution. The pH of the resultant solution was adjusted to 7.0 by adding 1M aqueous NaOH solution to obtain an aqueous solution (10 mM) containing the desired product (VI).

Example 2

Evaluation of Imaging Capability by MRI (1)

For the contrast agent as synthesized (prepared) in Example 1, evaluation of in vitro imaging capability by MRI was carried out with an aortic vascular section extirpated from a pig, as a specimen.

The aortic vascular section extirpated from a pig was spread in a rectangular shape measuring about 2 cm×3 cm to prepare a vascular section sample. The endothelial surface of the left half of the sample was exfoliated with a scalpel. The sample was then immersed in a 10 mM aqueous solution of the contrast agent for ten seconds. Following thorough washing with physiological saline solution, the sample was subjected to the evaluation by MRI as well as by visual observation.

Figure 2:
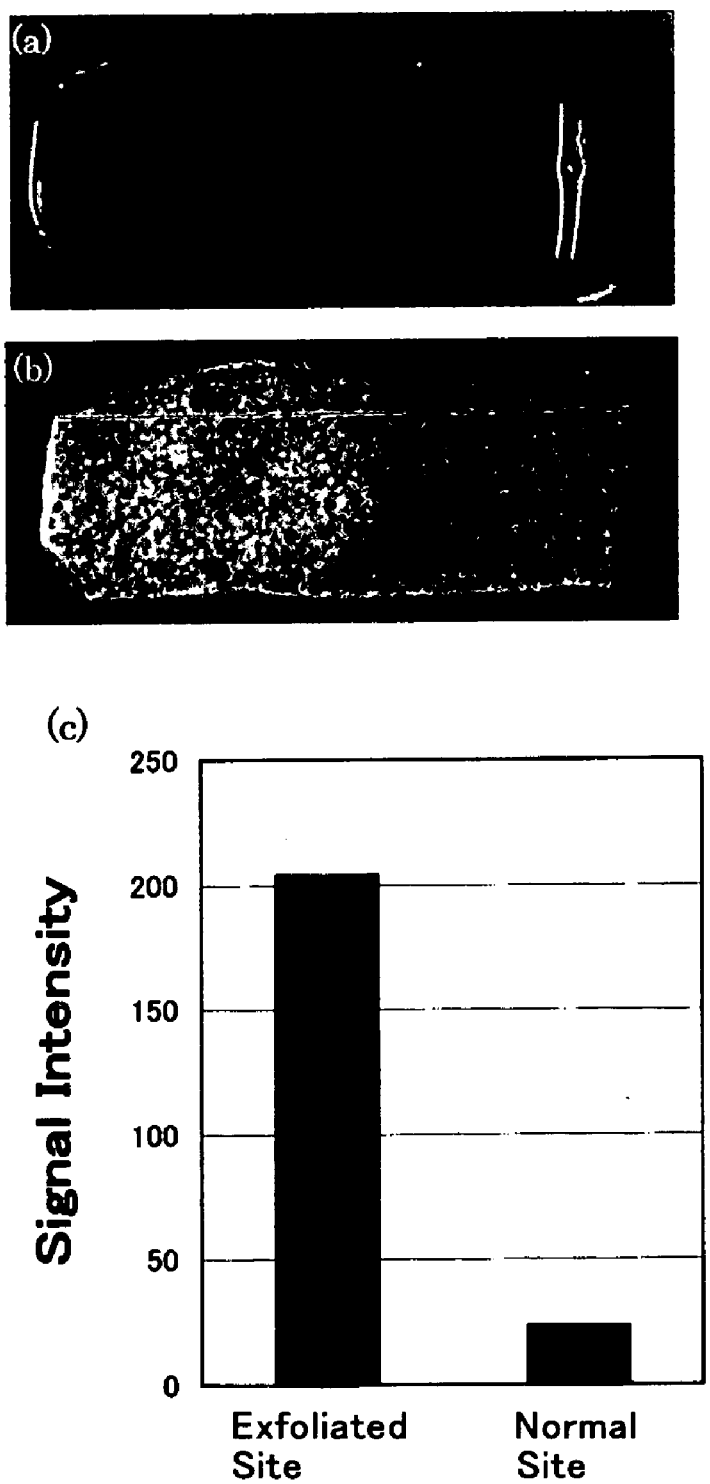
FIG. 2 shows the results of an experiment conducted to evaluate the imaging capability of an MRI contrast agent of the present invention, by using an aortic vascular section extirpated from a pig.

The results are shown in FIG. 2. FIG. 2 (A) is a picture taken with a digital camera, which corresponds to the visual observation. It was visually observed that the exfoliated endothelial site (the left half) was colored blue, suggesting accumulation of the contrast agent on the site. FIG. 2 (B) is an MRI image (by the T1 weighted spin echo method). FIG. 2 (C) graphically shows MRI signal intensities at the exfoliated endothelial site and the normal endothelial site, in which the MRI signal intensities are digitized with a computer-aided image analysis system (NIHImage). The signal intensity at the exfoliated endothelial site is about ten times as high as that at the normal endothelial site, demonstrating that the contrast agent of the present invention is capable of specifically binding to the exfoliated endothelial site thereby producing a clear image through the MRI signal.

Example 3

Evaluation of Imaging Capability by MRI (2)

The contrast agent of the present invention was evaluated for imaging capability by means of an ex vivo experiment using a living rat.

A balloon-tip catheter was passed through the left femoral artery of the rat to injure the carotid artery with the balloon. Then 2 ml of aqueous saline solution containing 24 mM of the contrast agent (EBDTPA-Gd prepared in Example 1) was injected to the rat through the right jugular vein. After a predetermined period of time (10, 30 or 120 minutes), the right carotid artery and the left carotid artery were extirpated, developed, washed with a physiological saline, and then subjected to evaluation by MRI. The MRI evaluation was carried out by imaging the extirpated carotid artery sections, under the condition of being added with one or two droplets of physiological saline solution, by the T1 weighted spin echo method.

Figure 3:
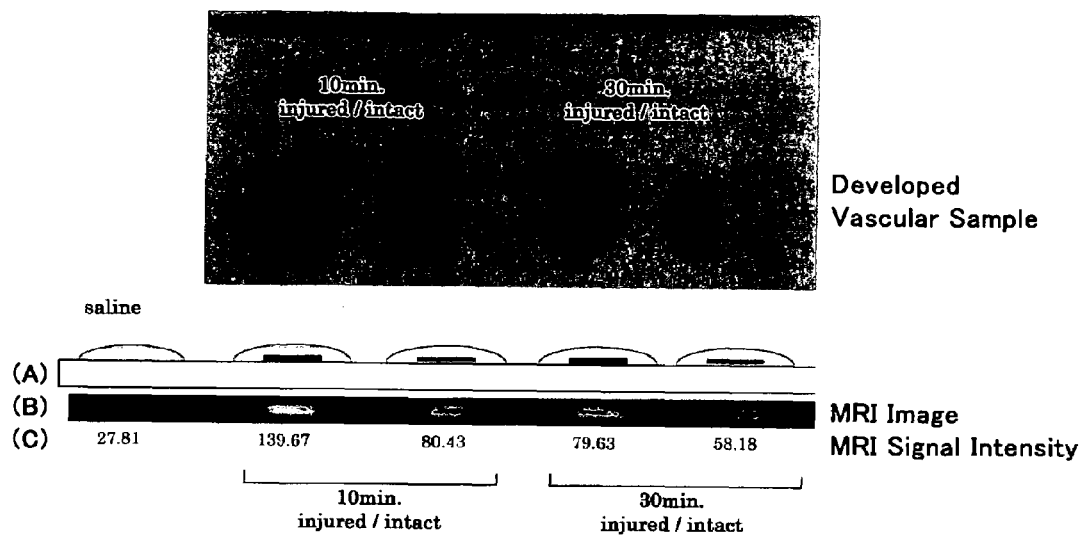
FIG. 3 shows the results of an experiment conducted to evaluate the imaging capability of the MRI contrast agent of the present invention, using a living rat.

The results are shown in FIG. 3. In FIG. 3, by "injured" is denoted the exfoliated endothelial site (the left carotid artery), which had been injured by the balloon, while "intact" denotes the normal endothelial site (the right carotid artery). The photographs of the developed vascular samples as presented in FIG. 3 reveal purple coloring with intensities corresponding to the MRI signal intensities described later. The pictures (A) as presented in FIG. 3 below the photographs of the developed vascular samples illustrate the states of the samples prepared for the study by MRI. As illustrated, each carotid artery section was developed on a glass plate and covered with one or two droplets of physiological saline solution, for the MRI study. (The leftmost picture of (A) shows a control composed of only physiological saline solution.) Below (A) in FIG. 3, there are shown MRI images (B) of the respective samples and digitized MRI signal intensities (C) (digitized with the computer-aided image analysis system, NIHImage, as in Example 2).

As seen from FIG. 3, the signal intensity of the injured site (the exfoliated endothelial site) is 1.74 times as high as that of the normal site after a lapse of ten minutes from the injection, demonstrating that the contrast agent of the present invention is capable of selectively detecting and imaging vascular exfoliated endothelial sites even in a living body. It is also seen that after a lapse of thirty minutes the signal intensities of the exfoliated endothelial site and the normal sites weakened and the difference in the signal intensity therebetween shortened and further that after 120 minutes there was observed no substantial difference in the signal intensity between the exfoliated site and the normal site, indicating that the contrast agent of the present invention can be rapidly excreted out of the body.

This was also verified by measuring Gd (gadolinium) content remaining in various organs of the rat, in which the measurement was carried out as follows: The rat was administered with 1 ml heparin and a blood sample was taken from the rat. Then physiological saline solution was circulated throughout the rat, and the various organs were extirpated from the rat. To each organ and the blood sample was added 3 ml nitric acid, followed by standing for one hour. The resultant was added with 25% hydrogen peroxide aqueous solution and then allowed to stand overnight at room temperature. The resultant solution was warmed and added with 6 ml water. The insolubles were removed by filtration, and the filtrate was analyzed by ICP.

Figure 4:
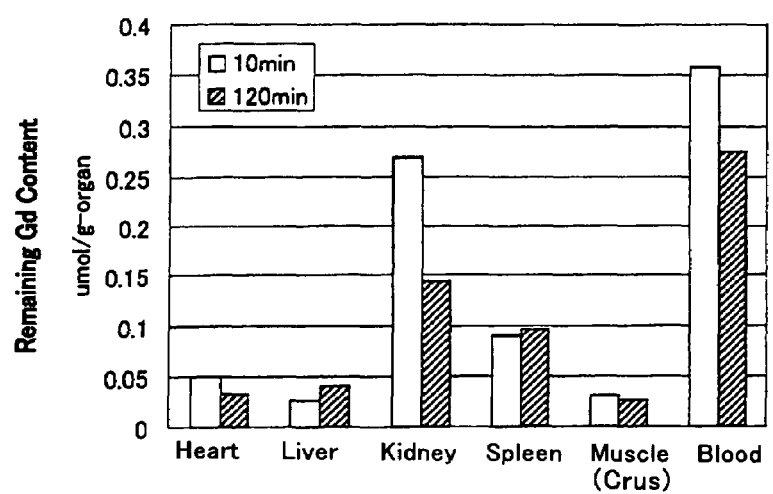
FIG. 4 shows the results of measurements of the Gd content, from the MRI contrast agent, remaining in various organs of a rat.

The results of the measurement are shown in FIG. 4. It can be seen from FIG. 4 that there was substantially no remaining Gd in organs other than the blood and kidney, suggesting that the contrast agent of the present invention can be mostly excreted as urine through the kidney. In fact, this was ascertained from the fact that, ten minutes after the administration of the contrast agent into the rat, the urine was colored purple due to the contrast agent.

Example 4

Evaluation of Imaging Capability by MRI (3)

This example is to evaluate the imaging capability of the contrast agent of the present invention by means of an in vivo experiment using a living rat.

Figure 5:
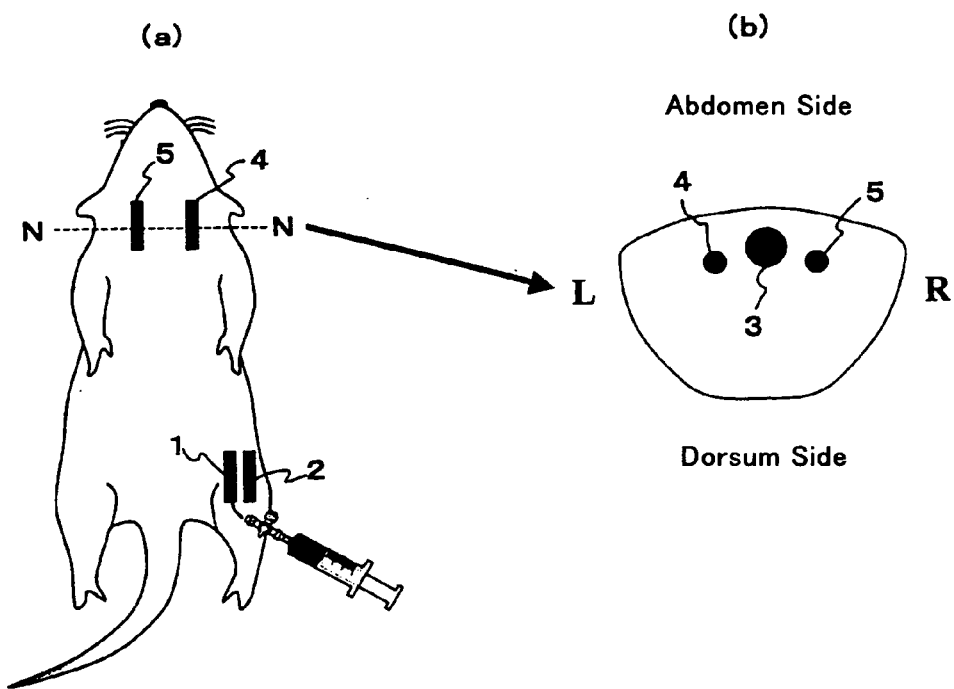
FIG. 5 illustrates the observation sites of a rat with which an in vivo experiment was carried out to evaluate the imaging capability of the MRI contrast agent of the present invention.

A rat (weighing about 300 g) was anesthetized with pentobarbital, and inserted with a balloon-tip catheter through the left femoral artery [FIG. 5 (a), 1]. The left common carotid artery was scraped by the balloon to injure the endothelia thereof. Then the rat was injected, through the left femoral vein [FIG. 5 (a), 2], with 2 ml (about 160 μM/kg) of physiological aqueous solution of the contrast agent as prepared in Example 1 (24 mM). At predetermined lapses of time, images were taken by MRI (the T1 weighted spin echo method) around the right and left common carotid artery [the cross section along the line N-N in FIG. 5 (a)]. The rat was supplementally anesthetized in order to keep it motionless during the imaging operation. For comparison, an evaluation experiment was also carried out in the same manner with a conventional agent, DTPA-Gd.

Figure 6:
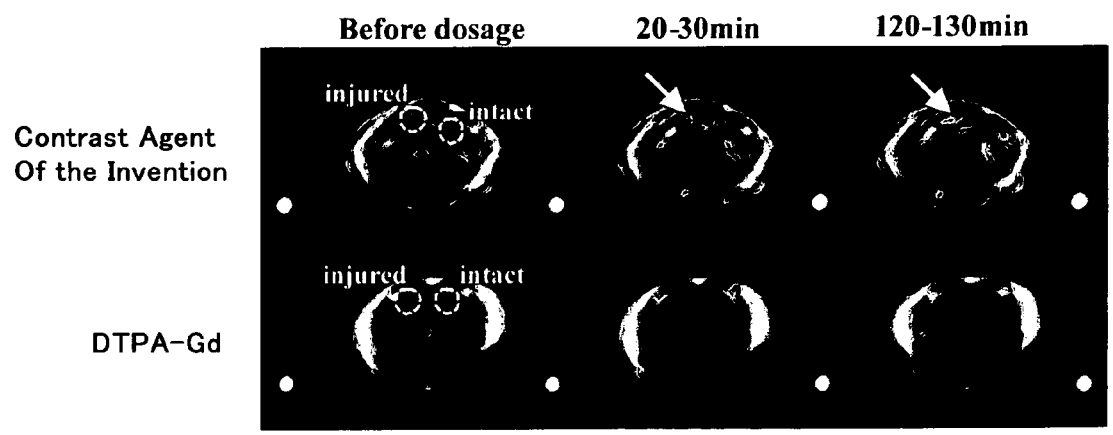
FIG. 6 shows MRI images of a rat taken using the MRI contrast agent of the present invention and a comparative MRI contrast agent.
Figure 7:
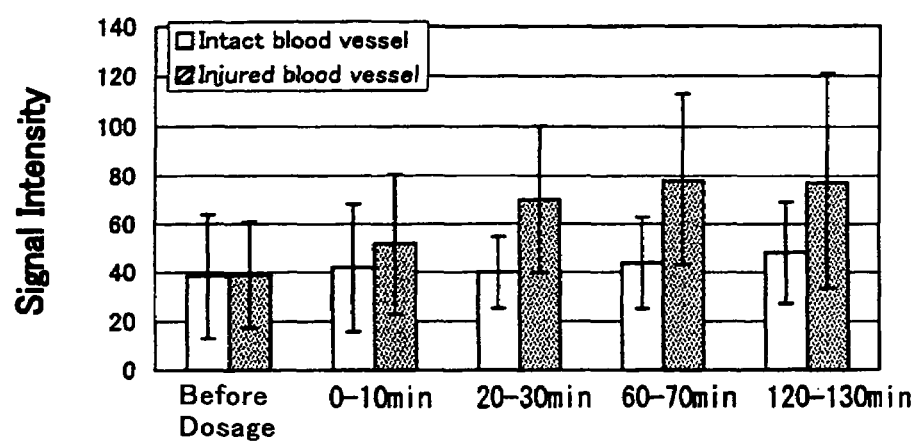
FIG. 7 shows graphical representations of digitized MRI signal intensities in the MRI imaging tests conducted on the rat using the MRI contrast agent and the comparative MRI contrast agent.
Figure 7:
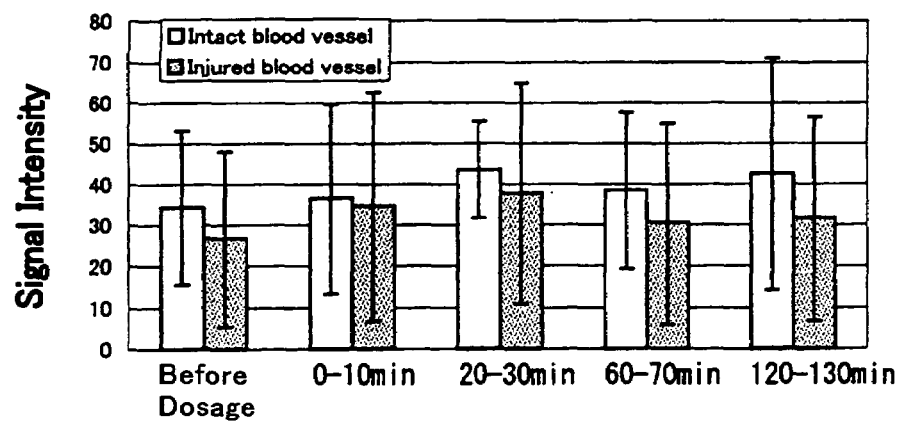

The results of the imaging operation are shown in FIG. 6 and FIG. 7. FIG. 6 shows the images of the rat taken in the vicinity of the common carotid artery at the cross section corresponding FIG. 5 (b). In FIG. 6, by "injured" is designated the left common carotid artery injured by the balloon, corresponding to 4 in FIG. 5 (b), while by "intact" is designated the right common carotid artery, which is normal and corresponds to 5 in FIG. 5 (b). The numeral 3 in FIG. 5 (b) denotes the bronchium. There was observed a clear MRI signal in the "injured" left common carotid artery when the contrast agent of the present invention was used (as can be seen from the clear white area indicated by an arrow), whereas no such signal was observed when the conventional contrast agent, DTPA-Gd, was used.

This fact is further demonstrated in FIG. 7 showing the time-varying MRI signal intensities of the injured common carotid artery and the normal common carotid artery, in which the signal intensities are digitized (in the same manner as in Example 2 and Example 3). Specifically, in the case where the contrast agent of the present invention was used, the MRI signal intensity for the injured left common carotid artery was higher than that for the normal right common carotid artery at ten minutes after the administration of the agent, and it increased with time, leveling off in about one hour after the administration. By contrast, with the conventional MRI agent, DTPA-Gd, no substantial difference in the signal intensity was observed between the injured common carotid artery and the normal common carotid artery, making it impossible to detect any injured sites.

INDUSTRIAL UTILIZABILITY

The MRI contrast agent of the present invention is a new type of contrast agent which is capable of directly detecting and imaging exfoliated vascular endothelial sites, thereby contributing to the early detection and early diagnosis of vascular diseases.

What us claimed is:

1. An MRI contrast agent which is expressed by the following chemical formula (VII):

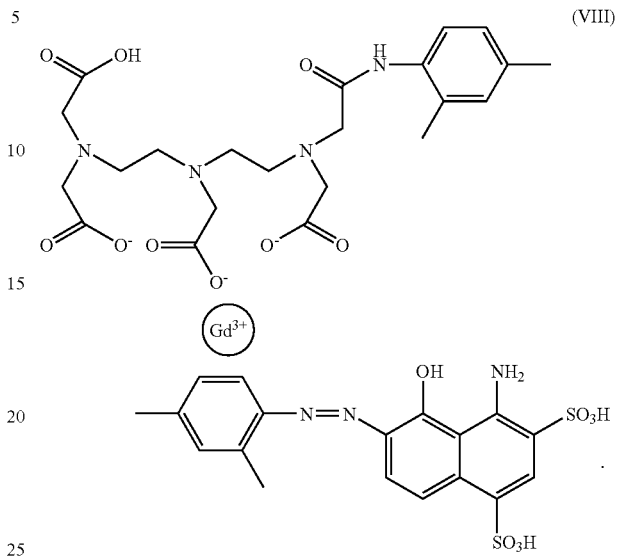

2. A method of MRI for selectively exfoliated vascular endothelial sites, comprising administering the MRI contrast agent of claim 1 and performing MRI imaging.

* * * * *